United States Patent [19]

Rempfler et al.

[11] 4,325,729

[45] Apr. 20, 1982

[54] HERBICIDAL AND PLANT GROWTH REGULATING PYRIDYLOXY-PHENOXY-PROPIONIC ACID DERIVATIVES

[75] Inventors: Hermann Rempfler, Ettingen; Rolf Schurter, Binningen; Werner Föry, Basel, all of Switzerland

[73] Assignee: Ciba-Geigy Corporation, Ardsley, N.Y.

[21] Appl. No.: 206,518

[22] Filed: Nov. 13, 1980

Related U.S. Application Data

[63] Continuation-in-part of Ser. No. 860,409, Dec. 13, 1977.

[51] Int. Cl.$^3$ .................... A01N 43/40; C07D 213/64
[52] U.S. Cl. ........................................ 71/94; 546/208; 546/281; 546/287; 546/288; 546/291; 546/300; 546/302
[58] Field of Search .................. 546/302, 300, 291; 71/94

[56] References Cited

U.S. PATENT DOCUMENTS

| | | | |
|---|---|---|---|
| 4,046,553 | 9/1977 | Takahashi et al. | 546/291 X |
| 4,133,675 | 1/1979 | Schurter et al. | 546/283 X |
| 4,233,054 | 11/1980 | Szczepanski et al. | 71/70 |
| 4,233,055 | 11/1980 | Martin | 71/76 |
| 4,233,056 | 11/1980 | Maier | 71/86 |
| 4,233,306 | 11/1980 | Böger et al. | 424/263 |
| 4,233,308 | 11/1980 | Kunz et al. | 424/279 |
| 4,244,962 | 1/1981 | Hubele et al. | 424/267 |
| 4,253,866 | 3/1981 | Schurter et al. | 71/94 |

FOREIGN PATENT DOCUMENTS 51-139627 12/1976 Japan.
51-142536 12/1976 Japan.
51-142537 12/1976 Japan.

*Primary Examiner*—Richard A. Schwartz
*Attorney, Agent, or Firm*—Frederick H. Rabin

[57] ABSTRACT

The present invention concerns new α-[4-(5'-trifluoromethyl-pyrid-2'-yl)oxy-phenoxy]-propionic-acid derivatives of the formula

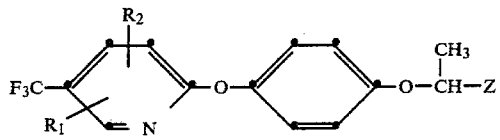

wherein
$R_1$ and $R_2$ independently are hydrogen, halogen, cyano or lower alkyl, and
Z is a radical —$COR_3$ or a 2-oxazoline group, whereby $R_3$ is the hydroxyl group or a salt form thereof, or is an ester, thioester, amide or hydrazide group on said propionic acid.

These new propionic acid derivatives have herbicidal and plant growth regulating activity and may be worked up into compositions containing them.

17 Claims, No Drawings

HERBICIDAL AND PLANT GROWTH REGULATING PYRIDYLOXY-PHENOXY-PROPIONIC ACID DERIVATIVES

CROSS-REFERENCE TO RELATED APPLICATION

This is a continuation-in-part of our application Ser. No. 860,409, filed Dec. 13, 1977 sending.

DETAILED DISCLOSURE

The present invention relates to novel pyridyloxy-phenoxy-propionic acid derivatives which are effective as herbicides and as agents regulating plant growth, to processes for producing them, to compositions containing these novel compounds as active substances, and to the use of the novel active substances or of the compositions containing them for selectively combating weeds in crops of cultivated plants or for regulating plant growth.

The novel active substances correspond to the formula I

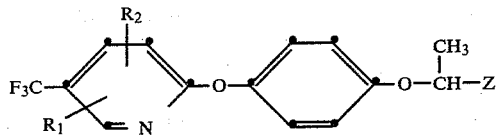

wherein $R_1$ and $R_2$ independently of one another are each hydrogen, halogen, the cyano group or a $C_1$—$C_4$—alkyl group, and Z is a radical —$COR_3$, $R_3$ is the hydroxyl group, or one of the radicals

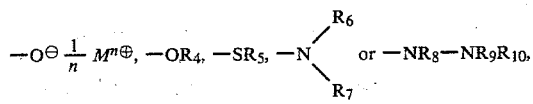

$R_4$ is $C_1$–$C_{18}$-alkyl which can be unsubstituted or substituted by halogen, cyano, $C_1$–$C_4$-alkoxy, $C_1$–$C_4$-alkylthio, carboxy, $C_1$–$C_4$-alkoxycarbonyl, $C_3$–$C_{12}$-cycloalkyl, phenyl or naphthyl; $C_3$–$C_{12}$-cycloalkyl, $C_3$–$C_8$-alkenyl which can be unsubstituted or substituted by halogen, $C_3$–$C_8$-alkynyl or phenyl which is unsubstituted or monosubstituted by halogen, $C_1$–$C_4$-alkyl, $C_1$–$C_4$-alkoxy, $C_1$–$C_4$-alkylthio, cyano or nitro, $R_5$ is $C_1$–$C_{18}$-alkyl which can be unsubstituted or substituted by $C_3$–$C_{18}$-cycloalkyl, $C_1$–$C_4$-alkoxycarbonyl, halogen, cyano, phenyl or naphthyl; $C_3$–$C_{12}$-cycloalkyl, $C_3$–$C_8$-alkenyl or phenyl which is unsubstituted or monosubstituted by halogen, $C_1$–$C_4$-alkyl, $C_1$–$C_4$-alkoxy, $C_1$–$C_4$-alkylthio, cyano or nitro, $R_6$ and $R_7$ independently of one another are each hydrogen or $C_1$–$C_4$-alkyl which can be optionally substituted by hydroxyl, cyano, $C_1$–$C_4$-alkoxycarbonyl or $C_1$–$C_4$-alkoxy; also $C_1$–$C_4$-alkoxy, $C_3$–$C_8$-alkenyl, $C_3$–$C_8$-alkynyl, hydroxyl, phenyl or benzyl, the phenyl rings being optionally mono- to trisubstituted by halogen, $C_1$–$C_4$-alkyl, alkoxy, alkylthio, cyano or nitro, or $R_6$ and $R_7$ together with the nitrogen atom to which they are bound form pyrrolidino or piperidino, $R_8$ is hydrogen, $C_1$–$C_4$-alkyl, phenyl or benzyl, $R_9$ and $R_{10}$ independently of one another are each hydrogen, $C_1$–$C_4$-alkyl, $C_2$–$C_4$-alkoxyalkyl, ($C_1$–$C_4$)-alkanoyl, benzoyl, or a phenyl ring which can be unsubstituted or monosubstituted by halogen, $C_1$–$C_4$-alkyl or $C_1$–$C_4$-alkoxy, or $R_9$ and $R_{10}$ together with the nitrogen atom to which they are bound form pyrrolidino or piperidino, $(1/n)M^{n\oplus}$ is the ion equivalent of an n-valent alkali metal ion or alkaline-earth metal ion, of a copper or iron ion, or is a quaternary ($C_1$–$C_5$)alkylammonium or hydroxy($C_1$–$C_5$)alkyl-ammonium group.

In this formula the quaternary ammonium groups or hydroxyammonium groups can contain up to 5 carbon atoms per alkyl moiety; preferred groups are the tetraethylammonium group and the dihydroxyethylammonium group. Chlorine is preferred among the halogen atoms. Particularly interesting compounds are those having an —$OR_4$ group for $R_3$, i.e. with the ester configuration —$COOR_4$.

It has already become known that specific 4-(pyrid-2-yloxy)-phenoxyalkanecarboxylic acids, or specific derivatives of these carboxylic acids, can be used as herbicides (see German Offenlegungsschrift No. 2,546,251, Japanese Kokai 51-139627, 51-142536 and 51-142537. The herbicidal action, particularly against weeds difficult to combat, is however not always satisfactory.

It has now been found that the trifluoromethylated novel pyridyloxy derivatives of the formula I according to the present invention surprisingly have a better herbicidal action, and can be used as herbicides for pre-emergence and postemergence application.

The active substances according to the invention also have favourable growth-regulating effects (growth inhibition). They inhibit in particular also the growth of dicotyledonous plants. Examples of the profitable application of the compounds according to the invention are: the reduction of vegetative growth in the case of soyabean plants and similar leguminosae, an effect which leads to an increase in the yield of these crops; the reduction of the undesirable growth of side shoots on tobacco plants, the leading shoots of which have been cut, an effect which promotes the formation of larger and better leaves; or the reduction of the growth of grass and of dicotyledonous plants, such as fruit trees, ornamental trees, shrubs and hedges, for the purpose of economising in the amount of cutting work.

The compounds of the present invention are negligibly toxic to warm-blooded animals, and application of the compounds presents no problems. The amount applied is between 0.06 and 5 kg per hectare.

The following compounds of the Formula I showed interesting results in green-house tests, when their herbicidal and plant-growth regulating properties were assessed:

The groups of compounds according to the formulae Ia, Ib and Ic

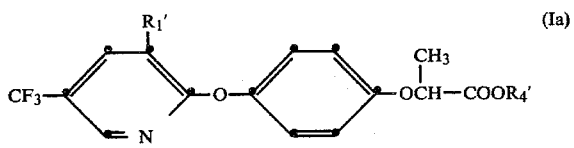

wherein $R_1'$ is hydrogen or halogen; and $R_4'$ is $C_1$–$C_{18}$-alkyl substituted by cyano or carboxyl;

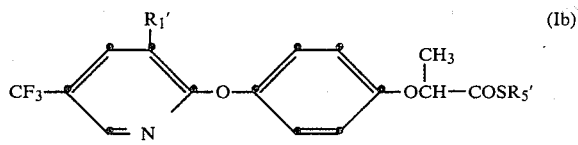

(Ib)

wherein $R_1'$ is hydrogen or halogen; $R_5'$ is $C_1$–$C_{18}$-alkyl substituted by halogen, cyano, $C_1$–$C_4$-alkoxycarbonyl or by phenyl which is unsubstituted or monosubstituted by halogen, $C_1$–$C_4$-alkyl, $C_1$–$C_4$-alkoxy, $C_1$–$C_4$-alkylthio, cyano or nitro;

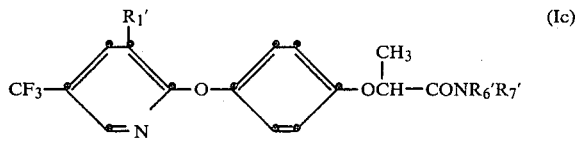

(Ic)

wherein $R_1'$ is hydrogen or halogen; $R_6'$ is $C_1$–$C_4$-alkyl substituted by cyano or by $C_1$–$C_4$-alkoxy, $C_3$–$C_4$-alkenyl or $C_3$–$C_4$-alkynyl; and $R_7'$ is hydrogen, $C_1$–$C_4$-alkyl or $C_3$–$C_4$-alkenyl.

The novel compounds of the formula I are produced by methods known per se.

One process for producing the pyridyloxy-phenoxy-propionic acid derivatives of the formula I comprises reacting a pyridyloxy-parahydroxy-phenyl ether of the formula II

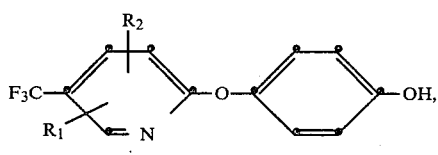

(II)

in the presence of a base, with a α-halogenocarboxylic acid derivative of the formula III

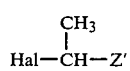

(III)

wherein Z' represents the groups

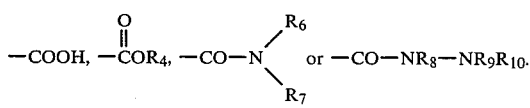

A second process comprises reacting an ortho-halogeno-pyridine of the formula IV

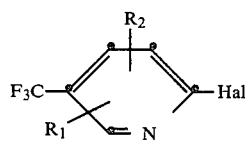

(IV)

with a para-hydroxyphenoxy-propionic acid derivative of the formula V

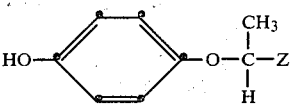

(V)

in the presence of a base.

If in these processes there is used as starting material of the formula III or V a carboxylic acid, this group can be subsequently converted into another derivative of the formula I as defined. Conversely, with the use for example of an ester of the formula III or V, the ester group can be subsequently converted by hydrolysis into the free carboxylic acid, and additionally into a salt, amide or hydrazide, or into a thiol ester or into another ester.

In the formulae II to V of the starting materials, the radicals $R_1$, $R_2$ and Z have the meanings given under the formula I, and "Hal" denotes a halogen atom, such as chlorine, bromine, etc.

The reactions mentioned can be performed in the presence or absence of solvents or diluents inert to the reactants.

Polar organic solvents are preferred, such as methyl ethyl ketone, acetonitrile, dimethylformamide, dimethylsulphoxide, etc. The reaction are between 0° and 200° C., and the reaction time, depending on the selected reaction temperature and on the solvent, is between ¼ hour and several days. The reaction is performed as a rule under normal pressure or under a slight excess pressure. Suitable bases (condensation agents) for the reaction are the customary bases, such as NaOH, KOH, NaOCH₃, K₂CO₃, NaH, Na₂CO₃, potassium-tert.-butylate, etc., and also organic bases.

Some of the starting materials of the formulae II to V are known. Starting materials not yet described of these formulae can be readily produced by conventional processes and techniques.

Substituted trifluoromethylpyridyloxy-parahydroxy-phenyl ethers of the formula II and trifluoromethyl-2-halogenopyridines of the formula IV can be easily produced from the corresponding hydroxycarbonyl- and trichloromethylpyridyl compounds, respectively, analogously to the methods of C. G. SWAIN et al., J.Am.-Soc. 82, 6101 (1960) and W. R. HASEK et al., J.Am. Soc. 82, 543 (1960).

Starting products of the formula V can be produced by reacting, for example, hydroquinonemonobenzyl ether with an α-halogenocarboxylic acid derivative, preferably with an ester of the formula III, and splitting the benzyl-phenyl ether bond by catalytic hydrogenation, e.g. with a palladium-on-charcoal catalyst, with the benzyl group being split off as toluene.

The starting products of the formula II can be obtained by reaction of hydroquinone with 2-halogeno-5-trifluoromethylpyridines in equimolecular amounts and in the presence of a base.

Carboxylic acid derivatives of the formula III are likewise known. As their simplest representatives, there may be mentioned, for example, α-chloropropionic acid and esters, thioesters, amides and hydrazides thereof.

The Examples which follow illustrate the production process according to the invention. Further novel active substances, produced in a corresponding manner, are subsequently listed. Temperature values are given in all cases in degrees Centigrade.

EXAMPLE 1

Methyl α-[4-(5'-trifluoromethyl-6'-chloropyrid-2'-yl)-oxy-phenoxy]-propionate

A solution of 19.6 g of methyl 2-(4'-hydroxy-phenoxy)-propionate in 20 ml of dimethylsulphoxide is added dropwise, with cooling, to a suspension of 2.4 g of sodium hydride in 30 ml of dimethylsulphoxide. After one hour's stirring, 23.8 g of 2,6-dichloro-3-trifluoromethyl-pyridine is added dropwise with cooling. After 2 hours, 500 ml of water is added, and extraction is performed with ether. The ether is dried with magnesium sulphate and removed by evaporation. The residue is distilled in a bulb tube at 130° C. (0.01 Torr). Recrystallisation from ether/petroleum ether yields 12 g of the product, which deliquesces from 50° C. upwards without any sharp melting point.

EXAMPLE 2

Isopropyl α-[4-(5'-trifluoromethyl-pyrid-2'-yl)-oxy-phenoxy]-propionate

A solution of 22.4 g (0.1 mole) of isopropyl 2-(4'-hydroxy-phenoxy)-propionate in 20 ml of dimethylsulphoxide is added dropwise, with cooling, to a suspension of 2.4 g (0.1 mole) of sodium hydride in 30 ml of dimethylsulphoxide. After a stirring time of one hour, 16.5 (0.1 mole) of 2-fluoro-5-trifluoromethylpyridine is added. After 2 hours, an addition of 500 ml of water is made, and the mixture is extracted with ether. The ether is dried and removed by evaporation and the oily residue is distilled under high vacuum to yield 31.6 g of the product; this has a boiling point of 100°–105° C. at 0.008 Torr and a refractive index $n_D^{30}$ of 1.4955.

EXAMPLE 3

Methyl α-[4-(5'-trifluoromethyl-pyrid-2'-yl)-oxy-phenoxy]-propionate

A solution of 19.6 g (0.1 mole) of methyl 2-(4'-hydroxyphenoxy)-propionate in 20 ml of dimethylsulphoxide is added dropwise, with cooling, to a suspension of 2.4 g (0.1 mole) of sodium hydride in 30 ml of dimethylsulphoxide. After one hour's stirring, 18.1 g (0.1 mole) of 2-chloro-5-trifluoromethyl-pyridine is added. The reaction mixture is stirred for 2 hours at room temperature; an addition of 500 ml of water is made, and the mixture is extracted with ether. The ether is dried with magnesium sulphate and removed by evaporation. The oily residue is distilled under high vacuum to yield 28.2 g of product having a boiling point of 110° C. at 0.01 Torr and a refractive index $n_D^{25}$ of 1.5056.

EXAMPLE 4

α-[4-(5'-Trifluoromethyl-pyrid-2'-yl)-oxy-phenoxy]-propionic acid 34 g of methyl α-[4-(5'-trifluoromethyl-pyrid-2'-yl)-oxyphenoxy]-propionate is heated in 100 ml of 2 N sodium hydroxide solution at 60° for 2 hours. After cooling, the reaction mixture is acidified with concentrated hydrochloric acid, and extracted with chloroform. The chloroform is dried with sodium sulphate and removed by evaporation. Recrystallisation from a mixture of carbon tetrachloride and hexane yields 25.3 g of the product having a melting point of 90°–94° C.

EXAMPLE 5

Ethyl α-[4-(5'-trifluoromethyl-pyrid-2'-yl)-oxy-phenoxy]-propionate 65 g of α-[4-(5'-trifluoromethyl-pyrid-2'-yl)-oxy-phenoxy]-propionic acid in 60 ml of thionyl chloride is heated at 60° C. for 4 hours; and the solution is then concentrated in vacuo. The remaining oil is dissolved in 500 ml of toluene, and 20 ml of ethanol is added. There is then added dropwise at 40° C. 25 g of triethylamine. The reaction mixture is cooled after 2 hours; the triethylamine hydrochloride which has precipitated is filtered off, and the filtrate is concentrated in vacuo. The oily residue is distilled under high vacuum to yield 48 g of the product having a boiling point of 103°–107° C. at 0.008 Torr and a refractive index $n_D^{25}$ of 1.5013.

EXAMPLE 6

Methyl α-[4-(5'-trifluoromethyl-pyrid-2'-yl)-oxy-phenoxy]-thiolpropionate 4.8 g of methylmercaptan is introduced into a solution of 34.5 g of α-[4-(5'-trifluoromethyl-pyrid-2'-yl)-oxy]-phenoxy-propionic acid chloride in 200 ml of toluene. There is simultaneously added dropwise 10.1 g of triethylamine dissolved in 50 ml of toluene. After introduction of the methylmercaptan, the reaction mixture is stirred for 1 hour at 25° C. and then for 2 hours at 35°–40° C. After the addition of 100 ml of water, the phases are separated; the toluene is dried with magnesium sulphate and removed by evaporation to leave as residue 24.8 g of the product having the refractive index $n_D^{25}$ of 1.5024.

EXAMPLE 7

Allyl α-[4-(5'-trifluoromethyl-pyrid-2'-yl)-oxy-phenoxy]-thiolpropionate 7.4 g of allylmercaptan is added to a solution of 34.5 g of α-[4-(5'-trifluoromethyl-pyrid-2'-yl)-oxy-phenoxy]-propionic acid chloride, and then 10.1 g of triethylamine in 50 ml of toluene is added dropwise. After one hour's stirring at 25° C., the reaction mixture is heated at 40° C. for 2 hours. After cooling, there is added 100 ml of water; the phases are separated, the toluene phase is dried with magnesium sulphate and concentrated by evaporation to leave as residue the oily product having a refractive index $n_D^{30}$ of 1.5018.

EXAMPLE 8

α-[4-(5'-Trifluoromethyl-pyrid-2'-yl)-oxy-phenoxy]-propionic acid ethylamide

A mixture of 10.1 g of triethylamine and 4.5 g of ethylamine is added dropwise, with cooling, to a solution of 34.5 g of α-[4-(5'-trifluoromethyl-pyrid-2'-yl)-oxy-phenoxy]-propionic acid chloride in 200 ml of toluene. After 2 hours, the triethylamine hydrochloride is filtered off and the toluene is removed by evaporation. The residue is recrystallised from ether/petroleum ether to yield 21.7 g of product with a melting point of 68°–73° C.

In a manner corresponding to that described in these Examples, the following compounds were obtained:

EXAMPLE 9

Cyanomethyl α-[4-(3'-chloro-5'-trifluoromethyl-pyridyl-2'-oxy)-phenoxy]-propionate, $n_D^{30}$ 1.5195.

EXAMPLE 10

(2''-Cyanoethyl) α-[4-(3'-chloro-5'-trifluoromethyl-pyridyl-2'-oxy)-phenoxy]-propionate, m.p. 87°–80° C.

EXAMPLE 11

(Methoxycarbonylmethyl)-α-[4-(3'-chloro-5'-trifluoromethyl-pyridyl-2'-oxy)-phenoxy]-thiopropionate, $n_D^{30}$ 1.5125.

EXAMPLE 12

Benzyl-α-[4-(3'-chloro-5'-trifluoromethyl-pyridyl-2'-oxy)-phenoxy]-thiolpropionate, $n_D^{30}$ 1.5667.

EXAMPLE 13

(Methoxycarbonyleth-1''-yl)-α-[4-(3'-chloro-5'-trifluoromethylpyridyl-2'-oxy)-phenoxy]-thiolpropionate, $n_D^{30}$ 1.5295.

EXAMPLE 14

(2-Methoxyethylamido)-α-[4-(3'-chloro-5'-trifluoromethylpyridyl-2'-oxy)-phenoxy-propionate, m.p. 110°–111° C.

EXAMPLE 15

Methyl α-[4-(5'-trifluoromethyl-3'-chloropyrid-2-yl)-oxy-phenoxy]-propionate.

EXAMPLE 16

Methyl α-[4-(5'-trifluoromethyl-3'-chloropyrid-2-yl)-oxy-phenoxy]thiolpropionate.

EXAMPLE 17

Methyl α-[4-(5'-trifluoromethyl-4'-chloropyrid-2-yl)-oxy-phenoxy)-propionate.

EXAMPLE 18

Ethyl α-[4-(5'-trifluoromethyl-4'-methyl-pyrid-2'-yl)oxy-phenoxy]-propionate.

EXAMPLE 19

Ethyl α-[4-(5'-trifluoromethyl-6'-methyl-pyrid-2'-yl)-oxy-phenoxy]-propionate.

EXAMPLE 20

Isobutyl α-[4-(5'-trifluoromethyl-6'-cyanopyrid-2'-yl)-oxy-phenoxy]-propionate.

EXAMPLE 21

α-[4-(5'-trifluoromethyl-6'-methyl-pyrid-2'-yl)-oxy-phenoxy]-propionic acid ethylamide.

EXAMPLE 22

2-[4'-(5'-trifluoromethyl-pyrid-2'-yl-oxy)-phenoxy]-ethyl-(1)-oxazoline of the formula

Further the derivatives of the formula I:

(a) Esters of α-[4-(5'-trifluoromethylpyrid-2'-yl)-oxyphenoxy]-propionic acid of the formula

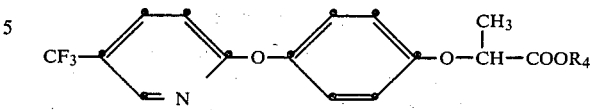

wherein R₄ is: n-propyl, iso-butyl, sec.-butyl, 2-chloroethyl, 2-methoxyethyl, 2-ethylthioethyl, 1-(methoxycarbonyl-1)-ethyl, pentyl-3, cyclopentyl, benzyl, 4-chlorobenzyl, phenylethyl, phenyl, p-tolyl, m-anisyl, cyclopentylmethyl, 2,2,2-trichloroethyl, tetrahydrofurfuryl, 2-buten-1-yl, allyl, propargyl, 2-cyanoethyl, cyclopropyl or methallyl.

(b) Esters of the corresponding thiolpropionic acid of the formula

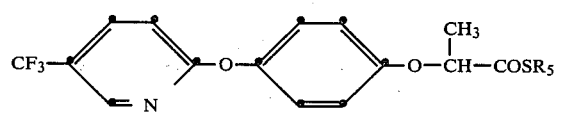

wherein R₅ ist: ethyl, butyl, methoxycarbonylmethyl, octyl, benzyl or ethoxycarbonylmethyl.

(c) Amides and hydrazides of α-[4-(5'-trifluoromethyl pyrid-2'-yl)-oxy-phenoxy]-propionic acid amide (NH₂), methylamide, dimethylamide, isopropylamide, 3-pentylamide, 2-chloroethylamide, allylamide, N-hydroxy-N-methylamide, N-ethoxy-N-methylamide, propargylamide, benzylamide, anilide, 4-ethoxycarboynylanilide, 1,1-dimethylpropargylamide, 1-methylpropargylamide, cyclopropylamide, cyclopropylmethylamide, 2-hydroxyethylamide, 2-methoxyethylamide, ethoxycarbonylmethylamide and 1-methyl-1-cyanoethylamide, α-[4-(5'-trifluoromethyl-pyrid-2'-yl)-oxyphenoxy]-propionyl-morpholine
-piperidine
-2-methylpiperidine,
as well as the hydrazide, N'-ethylhydrazide and N',N'-dimethylhydrazide of α-[4-(5'-trifluoromethylpyrid-2'-yl)-oxyphenoxy]-propionic acid. These pyridyloxy-phenoxy-propionic acid derivatives of the Formula I are stable compounds which are soluble in customary organic solvents, such as alcohols, ethers, ketones, dimethylformamide, dimethylsulphoxide, etc.

The compositions according to the invention are produced in a manner known per se by the intimate mixing and grinding of active substances of the general formula I with suitable carriers and/or distributing agents, optionally with the addition of anti-foaming agents, wetting agents, dispersing agents and/or solvents all inert to the active substances. The active substances can be obtained and used in the following forms:
  solid preparations:
    dusts, scattering agents, granules (coated granules, impregnated granules and homogeneous granules);
  water-dispersible concentrates of active substance:
    wettable powders, pastes, emulsions and emulsion concentrates;
  liquid preparations:
    solutions.

The concentration of active substance in the compositions according to the invention is 1 to 80% by weight, and can be optionally lower on application, such as about 0.05 to 1%.

Other biocidal active substances or agents can be added to the described compositions according to the invention. Thus, to widen their sphere of action, the novel composition can contain, besides the stated compounds of the general formula I, e.g. insecticides, fungicides, bactericides, fungiststics, bacteriostatics, nematocides of further herbicides.

GRANULATE

The following substances are used to produce a 5% granulate:
5 parts of one of the active substances of the formula I,
0.25 part of epichlorohydrin,
0.25 parts of cetyl polyglycol ether,
3.50 parts of polyethylene glycol, and
91 parts of kaolin (particle size: 0.3–0.8 mm).

The active substance is mixed with the epichlorohydrin and dissolved in 6 parts of acetone; polyethylene glycol and cetyl polyglycol ether are then added. The solution thus obtained is sprayed onto kaolin, and the acetone is subsequently evaporated off.

WETTABLE POWDER

The following constituents are used to produce (a) a 70% wettable powder and (b) a 10% wettable powder:

(a)

70 parts of one of the active substances of the formula I,
5 parts of sodium dibutylnaphthyl sulphonate,
3 parts of naphthalenesulphonic acid/phenolsulphonic acid/formaldehyde condensate 3:2:1,
10 parts of kaolin, and
12 parts of Champagne chalk;

(b)

10 parts of methyl α-[4-(5'-trifluoromethylpyrid-2'-yl)oxyphenoxy]-propionate,
3 parts of a mixture of the sodium salts of saturated fatty alcohol sulphates,
5 parts of naphthalenesulphonic acid/formaldehyde condensate,
82 parts of kaolin.

The given active substance is absorbed onto the appropriate carriers (kaolin and chalk), and subsequently mixed and ground with the other constituents. There are obtained wettable powders having excellent wetting and suspension properties. It is possible to prepare from such wettable powders, by dilution with water, suspensions having a content of active substance of 0.1–8%, which are suitable for combating weeds in crops of cultivated plants.

PASTE

The following substances are used to produce a 45% paste:
45 parts of methyl α-[4-(5'-trifluoromethyl-pyrid-2'-yl)oxyphenoxy]-propionate, or of another of the stated active substances of the formula I,
5 parts of sodium aluminium silicate,
14 parts of cetyl polyglycol ether having 8 moles of ethylene oxide,
1 part of oleyl polyglycol ether having 5 moles of ethylene oxide,
2 parts of spindle oil,
10 parts of polyethylene glycol, and
23 parts of water.

The active substance is intimately mixed and ground, in suitable devices, with the additives to obtain a paste from which can be prepared, by dilution with water, suspensions of the desired concentration.

EMULSION CONCENTRATE

The following substances are used to produce a 25% emulsion concentrate:
25 parts of methyl α-[4-(5'-trifluoromethyl-pyrid-2'-yl)-oxyphenoxy]-thiolpropionate, or of another of the stated active substances of the formula I,
5 parts of a mixture of nonyl phenol polyoxyethylene and calcium dodecylbenzene sulphate,
35 parts of 3,3,5-trimethyl-2-cyclohexen-1-one, and
35 parts of dimethylformamide.

This concentrate can be diluted with water to give emulsions of a suitable concentration, e.g. 0.1 to 10%. Such emulsions are suitable for combating weeds in crops of cultivated plants.

The novel 4-pyridyloxy-phenoxy-propionic acids and their derivatives of the formula I, and also the compositions which contain them, have an excellent selective herbicidal action against weeds in the widest variety of crops of cultivated plants. They likewise have a plant-growth-regulating action.

Although the novel active substances of the formula I are effective with both pre-emergence and post-emergence application, they are, compared with many known phenoxyphenoxy herbicides, distinguished with pre-emergence application by their excellent activity; however, their post-emergence application is also of interest.

Preferably, the novel active substances are applied, formulated for example as a 25% wettable powder or for example as a 20% emulsifiable concentrate and diluted with water, to the crops of plants after emergence.

Herbicidal action on application of the active substances after emergence of the plants (post-emergence)

Various cultivated plants and weeds are grown from seed in pots in a greenhouse until they have reached the 4- to 6-leaf stage. The plants are then sprayed with aqueous active-substance emulsions (obtained from a 20% emulsifiable concentrate) in different dosages. The treated plants are subsequently kept under optimum conditions of light, watering, temperature (22°–25° C.) and humidity (50–70% relative humidity). An evaluation of the tests is made, 15 days after tretment, using the 1–9 scale of values (see pre-emergence test).

The compounds of the Examples exhibited a good action in this test.

The following test methods serve to verify the suitability of the said compounds as herbicides (pre-emergence application) and as growth inhibitors:

Herbicidal action on application before emergence (pre-emergence)

Immediately after the sowing of the test plants in seed trays in a greenhouse, the surface of the soil is treated with an aqueous suspension of the active substances, obtained from a 25% wettable powder. Four different concentrations are used, corresponding to 4, 2, 1 and 0.5 kg of active substance per hectare. The seed trays are kept in the greenhouse at 22°–25° C. with 50–70% relative humidity, and the test is evaluated after 3 weeks, with the results being assessed on the basis of the 1–9 scale of values:
1 = plants not germinated or fully died off,
2–8 = intermediate stages of damage, 9=plants undamaged (as in the case of untreated control plants)

The following are used as test plants:

| | |
|---|---|
| Hordeum (barley) | Setaria italica |
| Triticum (wheat) | Echinochloa crus galli |
| Zea (maize) | Beta vulgaris |
| Sorghum hybr, (millet) | Sida spinosa |
| Oryza (rice) | Sesbania exaltlta |
| Glycine (soya bean) | Amaranthus retroflexus |
| Gossypim (cotton) | Sinapis alba |
| Avena fatua | Ipomoea pupurea |
| Lolium perenne | Galium aparine |
| Alopecurus myosuroides | Pastinaca sativa |
| Bromus tectorum | Rumex sp. |
| Cyperus esculentus | Chryanthemum leucum |
| Rottboellia exaltata | Abutilon sp. |
| Digitaria sanguinalis | Solanum nigrum |

The active substances tested were excellently effective against many weeds in this pre-emergence test.

Reduction of growth of grasses

Seeds of the grasses Lolium perenne, Poa pratensis, Festuca ovina and Dactylis glomerata are sown in a soil/peat/sand mixture (6:3:1) in plastic trays and watered in the usual manner. The emerged grasses are cut back each week to a height of 4 cm, and are sprayed 40 days after sowing and 1 day after the last cutting with aqueous spray liquors of an active substance of the formula I. The amount of active substance is equivalent to 5 kg of active substance per hectare. The growth of the grasses is evaluated 10 and 21 days after application.

Reduction of growth of cereals

Spring wheat (Triticum aestivum), spring barley (Hordeum vulgare) and rye (Secale) are sown in sterilised soil in plastic trays and are grown in a greenhouse. The shoots of the cereals are treated, 5 days after sowing, with a spray liquor of the active substance. This leaf application is equivalent to 6 kg of active substance per hectare. An evaluation is made after 21 days.

The tested active substances according to the invention produce an appreciable reduction in growth both of the grasses and of the cereals.

Reduction of the growth of undesirable side shoots on tobacco plants

Tobacco plants of the "Xanti" variety are grown in a greenhouse and are topped shortly before flowering (the leading shoots are cut off). One day after topping, 3 plants in each case are sprayed from above each with 10 ml of an aqueous preparation of a compound of the formula I. The selected concentrations of active substance are equivalent, in a normal plant population. To applied amounts of 12 kg of active substance/hectare, 6 kg of active substance/hectare and 3 kg of active substance/hectare, respectively. The inhibiting effect on the undesired growth of side shoots is evaluated 14 days after application of the preparations. The average length of the side shoots from the 6 uppermost leaf axils of all 3 plants are determined.

The plants treated with the compounds display no growth, or very little growth, of side shoots, whereas on the untreated control plants the side shoots have an average length of over 20 cm.

We claim:

1. A compound of the formula

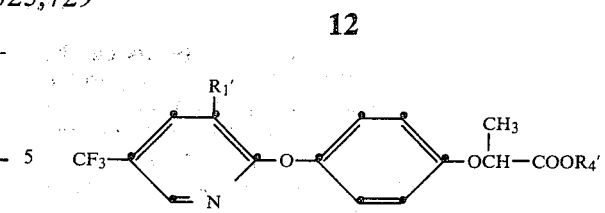

wherein $R_1'$ is hydrogen or halogen; and $R_4'$ is $C_1$–$C_{18}$-alkyl substituted by cyano.

2. Cyanomethyl-α-[4-(3'-chloro-5'-trifluoromethylpyrid-2'-yl)-oxyphenoxy]-propionate, according to claim 1.

3. (2-cyanoethyl-α-[4-(3'-chloro-5'-trifluoromethylpyrid-2'-yl)-oxyphenoxy]-propionate, according to claim 1.

4. A compound of the formula

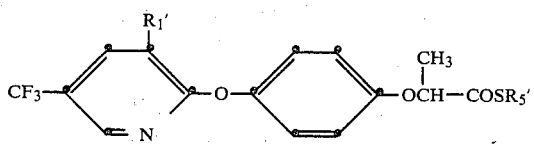

wherein $R_1'$ is hydrogen or halogen; and $R_5'$ is $C_1$–$C_{18}$-alkyl substituted by halogen, cyano, $C_1$–$C_4$-alkoxycarbonyl or by phenyl which is unsubstituted or monosubstituted by halogen, $C_1$–$C_4$-alkyl, $C_1$–$C_4$-alkoxy, $C_1$–$C_4$-alkylthio, cyano or nitro.

5. (Methoxycarbonylmethylthio)-α-[4-(3'-chloro-5'-trifluoromethylpyrid-2'-yl)-oxy-phenoxy]-propionate, according to claim 4.

6. (Methoxycarbonyleth-1''-ylthio)-α-[4-(3'-chloro-5'-trifluoromethylpyrid-2'-yl)-oxy-phenoxy]-propionate, according to claim 4.

7. Benzylthio-α-[4-(3'-chloro-5'-trifluoromethylpyrid-2'-yl)-oxy-phenoxy]-propionate, according to claim 4.

8. A compound of the formula

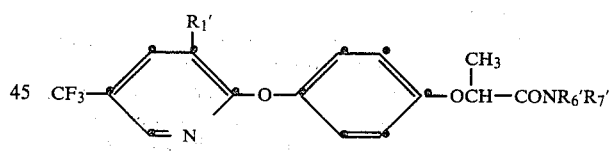

wherein $R_1'$ is hydrogen or halogen; $R_6'$ is $C_1$–$C_4$-alkyl substituted by cyano or by $C_1$–$C_4$-alkoxy, $C_3$–$C_4$-alkenyl or $C_3$–$C_4$-alkynyl; and $R_7'$ is hydrogen, $C_1$–$C_4$-alkyl or $C_3$–$C_4$-alkenyl.

9. (2-Methoxyethyl)-α-[4-(3'-chloro-5'-trifluoromethylpyrid-2'-yl)-oxy-phenoxy]-propionamide, according to claim 8.

10. A herbicidal composition which contains, as active ingredient, a herbicidally effective amount of a compound according to claim 1 and a carrier.

11. A herbicidal composition which contains as active ingredient a herbicidally effective amount of a compound according to claim 4 and a carrier.

12. A herbicidal composition which contains as active ingredient a herbicidally effective amount of a compound according to claim 8 and a carrier.

13. A method for selectively combating weeds in cultivated crops which comprises applying to the area to be treated a herbicidally effective amount of a compound according to claim 1.

14. A method according to claim 13 in which the compound is cyanomethyl-α-[4-(3'-chloro-5'-trifluoromethylpyrid-2'-yl)-oxyphenoxy]-propionate.

15. A method for selectively combating weeds in cultivated crops which comprises applying to the area to be treated a herbicidally effective amount of a compound according to claim 4.

16. A method according to claim 15 in which the compound is methoxyacetylthio-α-[4-(3'-chloro-5'-trifluoromethylpyrid-2'-yl)-oxyphenoxy]-propionate.

17. A method for selectively combating weeds in cultivated crops which comprises applying to the area to be treated a herbicidally effective amount of a compound according to claim 8.

* * * * *